US005792942A

United States Patent [19]
Hosokawa

[11] Patent Number: 5,792,942
[45] Date of Patent: Aug. 11, 1998

[54] APPARATUS FOR DETERMINING PROPERTIES OF SLURRY MATERIALS AND SLUDGE TREATING PROCESS

[75] Inventor: Kazutaka Hosokawa, Kanagawa, Japan

[73] Assignee: Koei Industry Co. Ltd., Kanagawa, Japan

[21] Appl. No.: 607,154

[22] Filed: Feb. 26, 1996

[30] Foreign Application Priority Data

Jul. 17, 1995 [JP] Japan ................... 7-180139

[51] Int. Cl.[6] ............................. G01N 11/00
[52] U.S. Cl. .................. 73/54.01; 73/863.84; 73/54.35
[58] Field of Search ................. 73/54.01, 54.28, 73/54.35, 863.84, 864.83

[56] References Cited

U.S. PATENT DOCUMENTS 4,269,064  5/1981  Johnson et al. ............... 73/422
4,544,489  10/1985  Campbell et al.
5,003,814  4/1991  Crawford et al. ............... 73/59

FOREIGN PATENT DOCUMENTS 7-136700  5/1995  Japan .

OTHER PUBLICATIONS

English language Abstract of Japanese Pat. Appln. No. 7-136700 published May 30, 1995.

*Primary Examiner*—Michael Brock
*Assistant Examiner*—Jay L. Politzer
*Attorney, Agent, or Firm*—Michael D. Bednarek; Kilpatrick Stockton LLP

[57] ABSTRACT

The present invention relates to a property determining apparatus for automatically determining in real time, properties of a slurry material such as of a sludge under treatment. The apparatus, being provided with a sampling cylinder 2, a quantitative sampling piston pair comprised of a rear piston 3 and a front piston 4, an air cylinder 5, a measurement tank 8, and a measuring means 10, is connected to a transfer pipe P and the like for a slurry material via a connecting opening 2w of the sampling cylinder 2. As a measuring operation, slurry material is first collected into the sampling cylinder 2 by a volume corresponding to the space S of the pistons 3,4 when the quantitative sampling piston pair is retracted from an initial position shown with a two-dot chain line, supplied to the measurement tank 8 when the space between the pistons are narrowed, then the properties of a slurry material is measured with the measuring means 10, and after that, the space of the pistons are returned to an original position so as to return the slurry material from the measurement tank into the sampling cylinder, and finally the quantitative sampling piston pair is returned to the original position to allow slurry material to be returned to the transfer pipe.

3 Claims, 9 Drawing Sheets

APPARATUS FOR DETERMINING PROPERTIES OF SLURRY MATERIALS AND SLUDGE TREATING PROCESS

This application is related to the subject matter disclosed in Applicant's co-pending U.S. patent application entitled "PROCESS AND APPARATUS FOR FILTRATE MEASUREMENT"; Ser. No. 08/590,111 filed on Jan. 23, 1996.

BACKGROUND OF THE INVENTION

1. Field of the Invention

The present invention relates to a technique of treating industrial waste water sludge, sewage sludge or slurry materials such as pulp slurry, particularly to a property determining apparatus for determining properties of such slurry material under treatment, as well as, to a sludge treating process using the same.

2. Description of the Prior Art

It is of general practice with industrial waste water sludge or sewage sludge to add a flocculating agent to adjust it to have a predetermined flocculation degree and to dehydrate the resulting sludge to provide a dehydrated cake, which is thermally disposed in the end or committed to those who commercially perform disposal. The running cost in such treatment system is greatly influenced by the amount of flocculating agent used and the dehydration efficiency of a dehydrating machine. While dehydrated cakes are, in the end, thermally disposed or committed to those who commercially perform disposal, the cost of fuel such as a heavy oil to be used for incineration or the cost per unit weight of the cakes for the commitment are greatly influenced by the water content of the cakes in these treatment methods.

Accordingly, it is important to optimize these cost influencing factors in aiming at realization of economical and energy-saving running of the system. In order to optimize the cost influencing factors, in other words to minimize the amount of flocculating agent used, to improve dehydration efficiency and further to reduce water content of the dehydrated cakes, it is essential to get real-time data on properties of the raw sludge before addition of the flocculating agent and flocculation degree of the sludge after addition of the flocculating agent and to accurately control the kind and amount of flocculating agent to be added based on these data.

However, there has been found so far no effective means for automatically processing these data on the sludge which is continuously treated, so that the treatment condition is determined depending on the experience of an operator under the present circumstances, which is far from ideal. Particularly, in the case where the condition in the sludge generating source is unstable and properties of the sludge to be treated often change with time, estrangement from the ideal condition tends to be much greater.

The present invention was accomplished based on such background, and it is an objective of the present invention to provide a property determining apparatus for automatically and real-time determination of properties of a slurry material such as of a sludge under treatment, as well as a sludge treating process employing the same.

SUMMARY OF THE INVENTION

First, the property determining apparatus according to the present invention is employed for collecting a slurry material directly, for example, from a transfer passage or a storage tank, constituting a slurry treating system, and for determining its properties such as solid content level and flocculation degree. For such purpose, the apparatus is provided with a sampling cylinder having a connecting opening at one end, a quantitative sampling piston pair consisting of a front and rear pistons which are accommodated in the sampling cylinder, means for operating the quantitative sampling piston pair, a measurement tank connected to the sampling means and measuring means incorporated into the measurement tank.

This property determining apparatus is used by connecting the connecting opening of the sampling cylinder to the slurry transfer passage and the like. Determination operation is started by retracting first the quantitative sampling piston pair positioned at an initial position with a predetermined sampling volume securing space being defined between the pistons. In the state where the quantitative sampling piston pair is at the initial position, generally, the rear piston is situated at the connecting opening of the sampling cylinder, whereas the front piston is protruded into the transfer passage and the like to be spaced from the rear piston maintaining the sampling volume securing space. Accordingly, if the quantitative sampling piston pair is retracted from the initial position, the slurry material can be collected into the sampling cylinder in an amount corresponding to the sampling volume securing space defined between the front piston and the rear piston.

If the space between the front piston and the rear piston is narrowed after the slurry material is collected into the sampling cylinder, the slurry material confined in the space defined by the front and rear pistons and the sampling cylinder is as such compressed to be forced out therefrom into the measurement tank. The measuring means is then actuated to determine property of the slurry material in the measurement tank. After completion of the measurement, the space between the front piston and the rear piston is widened to resume the original width. Thus, the slurry material flows back contrariwise out of the measurement tank into the space defined by the pistons and the sampling cylinder. If the quantitative sampling piston pair is returned to the initial position in this state, the slurry material is returned to the transfer passage and the like. After the slurry material is discharged from the sampling cylinder, as described above, the measurement tank and the sampling cylinder are cleaned by a cleaning mechanism, and thus one measurement cycle is completed.

According to the property determining apparatus of the present invention described above, a slurry material can be collected directly from a slurry transfer passage and the like any time as necessary to determine rapidly its properties. In other words, properties of the slurry material under treatment can be determined in real time. Further, in the property determining apparatus of the present invention, the sample slurry material can be returned as such to the source after completion of the measurement to cause no substantial change in the condition of the slurry material in the source. That is, measurement can be carried out without substantially affecting the treatment system.

The measuring means in the property determining apparatus is preferably of a structure in which property of the slurry material is determined based on the viscosity resistance. Such measuring means contains a rotor, and the property of the slurry material is designed to be determined by measuring viscosity resistance exerted to the rotor, when the rotor is rotated in the slurry material.

Meanwhile, in the property determining apparatus described above, the operating means is preferably of a fluid pressure operating body, such as a pneumatic operating body and a liquid pressure operating body, having an operation rod which advances and retracts along the axis of the sampling cylinder or an operating body employing a feed screw mechanism which is driven by a rotational driving source such as an electric motor. In the case where such operating body constitutes the operating means, as described above, the operation rod of the operating body is allowed to penetrate the rear piston, and the rear piston is adapted to be held as necessary by holding means fixed to the operation rod, while the front piston is unmovably connected to the operation rod of the operating body. This operating means has an operative structure in which the quantitative sampling piston pair is retracted with the rear piston being held by the holding means in the stroke that the slurry material is to be collected into the sampling cylinder; the quantitative sampling piston pair is retracted to a predetermined position where the rear piston is abutted against a stopper portion formed in the sampling cylinder to allow the holding means to release holding of the rear piston; in this state the front piston is further retracted so as to narrow the space between the rear piston and the front piston.

While the property determining apparatus is useful in determining properties of slurry materials in general, it is particularly useful in determining properties of a sludge under treatment. In addition, the apparatus enjoys high utility in determining in-line pulp concentration of a pulp slurry under treatment.

The sludge treating process according to the present invention, the process contains, basically, addition of a flocculating agent to a raw sludge collected from a raw sludge storage tank to adjust it to have a predetermined flocculation degree in a sludge flocculation reaction tank, and dehydration treatment of the resulting sludge over a dehydrator to form a dehydrated sludge cake; and additionally determination of solid content level of the raw sludge by the property determining apparatus, and controlling of the kind and amount of flocculating agent to be added in the sludge flocculation reaction tank by means of feed-forward control based on the determination result.

Feed-forward control of the amount and kind of flocculating agent to be added is carried out, for example, by providing a proportional control valve to a flocculating agent loader and automatically controlling this proportional control valve based on the measured value. Such control allows the flocculating agent to be added in a controlled manner under optimum conditions depending on the properties of the sludge on each occasion, even in the case where the properties of the raw sludge change with time, and thus not only the flocculating agent to be used can be held in a minimum necessary quantity, but also the sludge can be allowed to assume an optimum state of flocculation. If the flocculation state is optimized, dehydration efficiency can be also improved, so that power to be consumed for operating the dehydrator and the like can be also reduced. The improvement of dehydration efficiency also leads to reduction in the average water content of the dehydrated cakes, in turn, in the cost of treating the dehydrated cakes.

With respect to the sludge treating process described above, if flocculation degree of the sludge in the sludge flocculating reaction tank is also determined by the same property determining apparatus as described above, and feed-back control based on this measurement result is additionally employed so as to control the amount and kind of the flocculating agent to be added in the sludge flocculation reaction tank, more delicate control can be achieved, further optimizing the treatment condition.

While a plurality of sludge flocculation reaction tanks are sometimes employed in the sludge treating process described above, it is further preferred in such cases that the feed-forward control based on the determination result of the raw sludge solid content level is combined with the feed-back control based on the determination result of flocculation degree and other properties of the sludge after treatment in each sludge flocculation reaction tank.

BRIEF DESCRIPTION OF THE DRAWINGS

The features of the present invention that are believed to be novel are set forth with particularity in the appended claims. The invention, together with the objects and advantages thereof, may best be understood by reference to the following description of the presently preferred embodiments taken in conjunction with the accompanying drawings in which:

DETAILED DESCRIPTION OF THE PREFERRED EMBODIMENT

Figure 1:
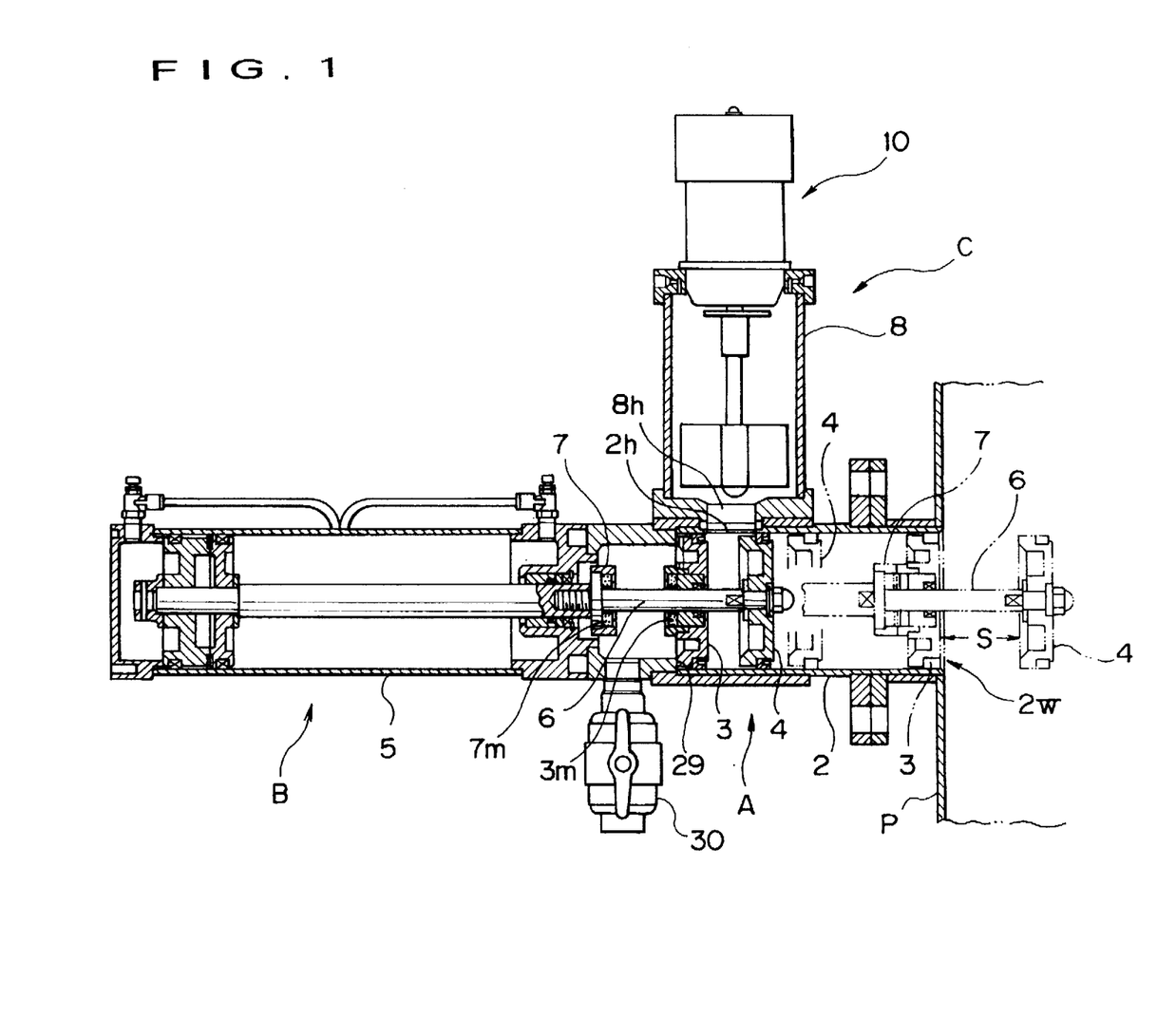
FIG. 1 shows a cross-sectional view of a property determining apparatus according to a first embodiment of the present invention.

Preferred embodiments of the present invention will be described below. Now, a first embodiment of the property determining apparatus will be described. As shown in FIG. 1, the property determining apparatus 1 according to the first embodiment is of a structure in which an operation block B and a measurement block C are connected axially and orthogonally to a sampling block A, respectively.

The sampling block A is composed of a sampling cylinder 2 having at one end a connecting opening 2w, and a quantitative sampling piston pair accommodated in the cylinder 2. The quantitative sampling piston pair consists of a rear piston 3 and a front piston 4 which literally form a pair. The front piston 4 of the quantitative sampling piston pair is fixedly connected to the distal end portion of an operation rod 6 of an air cylinder 5, which is operating means in the operation block B. Meanwhile, the operation rod 6 penetrates the rear piston 3, and the rear piston 3 is adapted to be connected to the operation rod 6 as necessary with the aid of holding means 7 fixed to the rod 6. The holding means 7 is of magnetic type. Specifically, a permanent magnet 7m is incorporated into the holding means 7, and another permanent magnet 3m is incorporated into the rear piston 3, so that the rear piston 3 may be held by the holding means 7 under the mutual attracting force of these two permanent magnets 7m,3m. Such quantitative sampling piston pair or the front and rear pistons 4,3 perform two actions: the front and rear pistons 4,3 advance and retract synchronously with a predetermined space being secured between them; only the front piston 4 advances and retracts with the rear piston 3 being immobilized. These two actions will be described later.

The measurement block C comprises a cylindrical measurement tank 8 and measuring means 10 incorporated into the tank 8. The measurement tank 8 has a communication opening 8h at the bottom and is connected to the sampling cylinder 2 with this communication opening 8h being aligned with a communication opening 2h defined on the barrel of the sampling cylinder 2.

Figure 2:
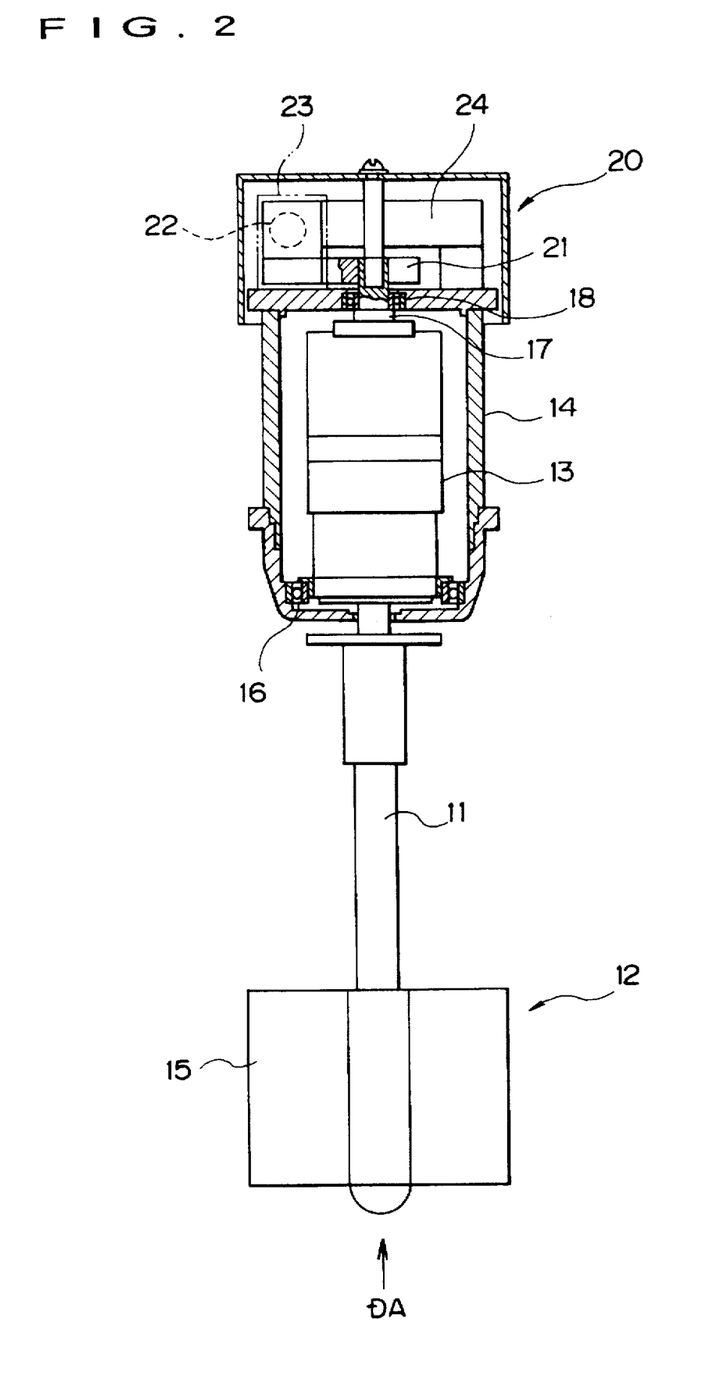
FIG. 2 shows a partially cross-sectional side view of a measuring means in the property determining apparatus shown in FIG. 1.

As the measuring means 10, there may be employed a sludge detector proposed already by the applicant of the present invention in Japanese Patent Application No. 307085/1993 (Laid-open Japanese Patent Application under Publication No. 136700/1995). To describe roughly the sludge detector, the measuring means 10 has an internal structure, as shown in FIG. 2, in which a rotor 12 is connected to an output shaft 11 of an electric motor 13 rotatably retained in a retaining case 14. The rotor 12 has three radial blades 15 each having a curved surface profile assuming an involute curve. Meanwhile, the electric motor 13 is retained in the retaining case 14 in such a way that a lower bearing 16 retains a housing of the electric motor 13 on lower outer circumference and that an upper bearing 18 supports an auxiliary member 17 connected to the top of the housing of the electric motor 13. Thus, the electric motor 13 is retained in the retaining case 14 to be rotatable freely in the case 14. A detecting section 20 is provided on the top of the retaining case 14 which retains the electric motor 13 therein as described above.

Figure 3:
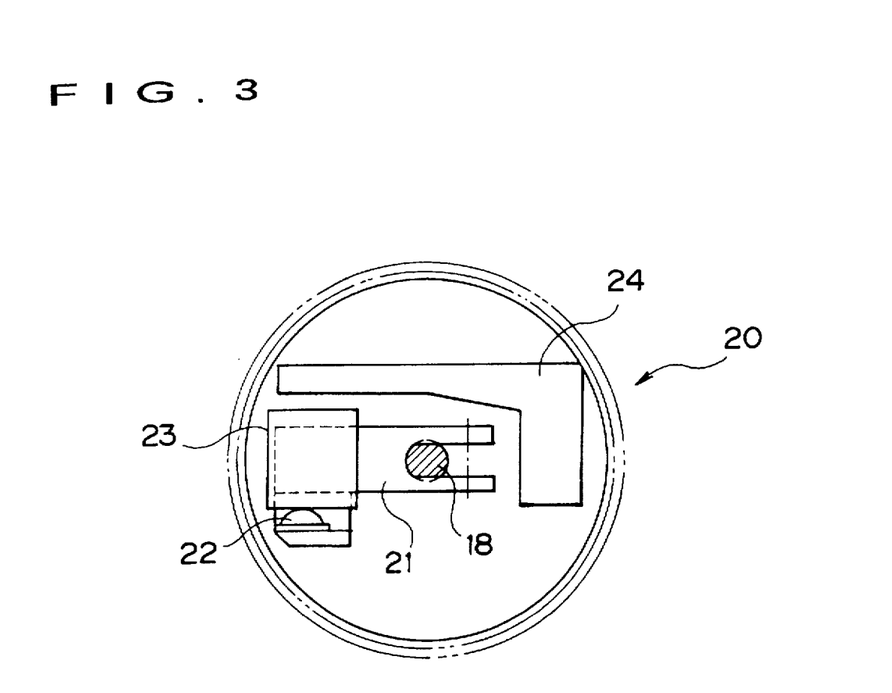
FIG. 3 shows a structural view of a detecting section in the measuring means shown in FIG. 2.
Figure 4:
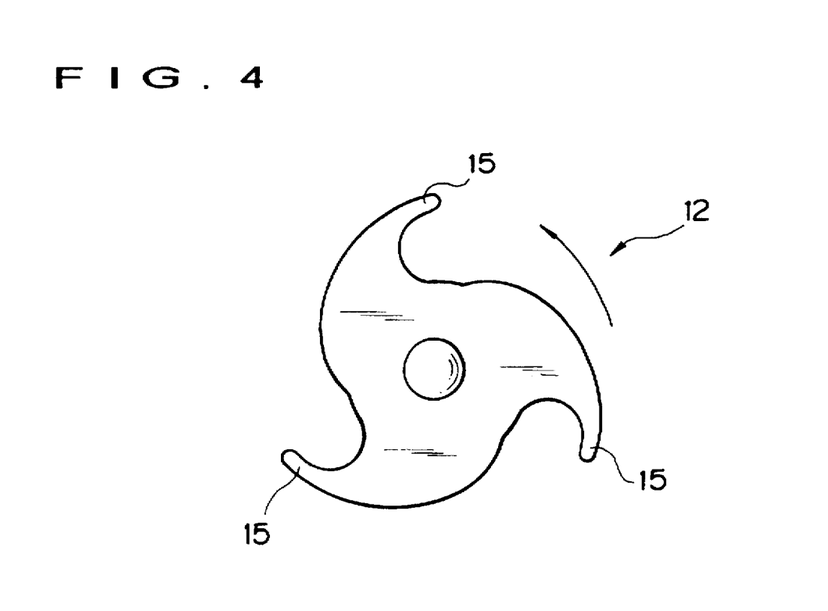
FIG. 4 shows a bottom plan view of a rotor in view DA in FIG. 2.
Figure 5:
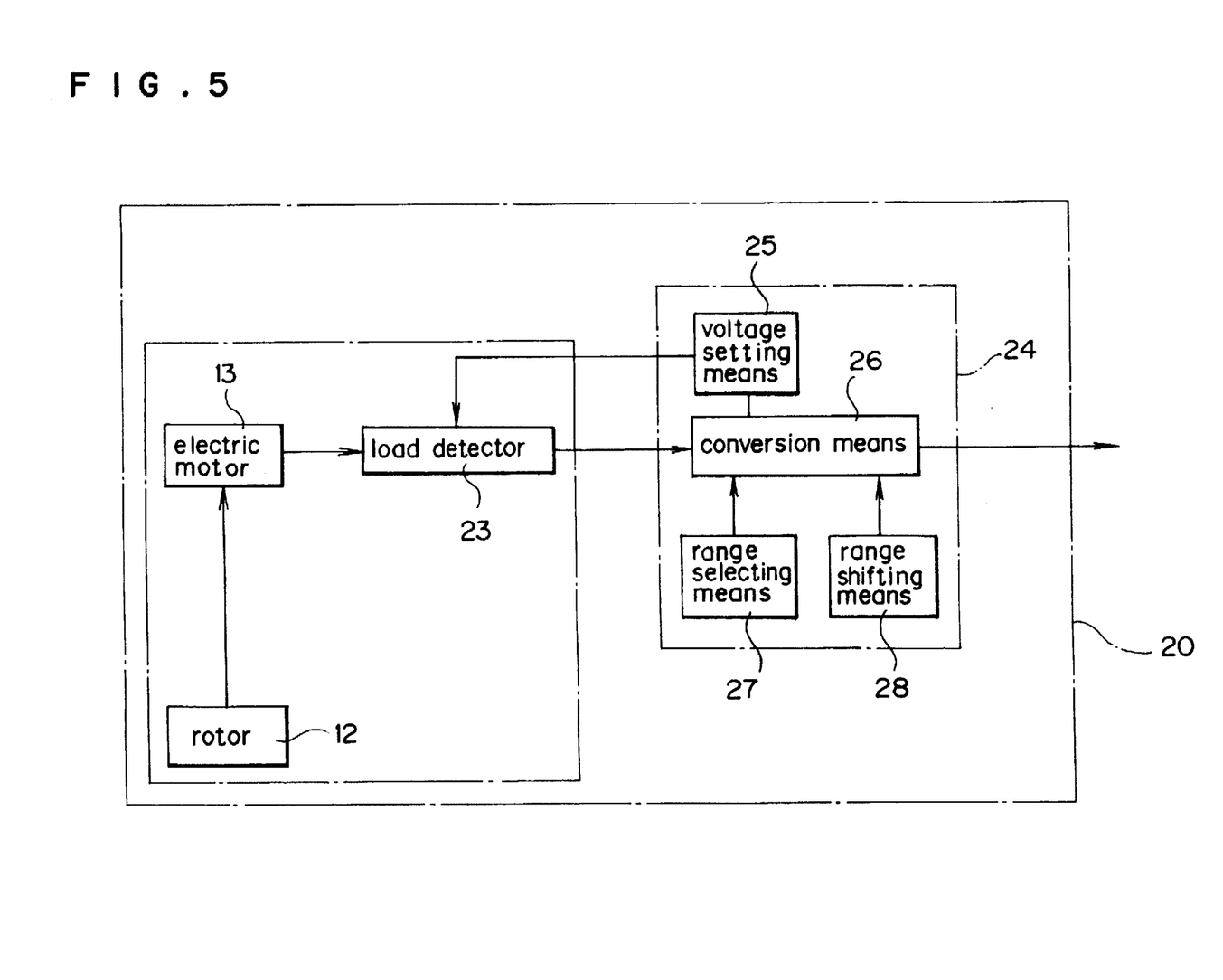
FIG. 5 shows a block diagram of the measuring means shown in FIG. 2.

This detecting section 20 detects viscosity resistance of a slurry material, as a reaction force exerted upon the motor 13, when the rotor 12 is rotated in the slurry material as will be described later. Accordingly, as shown in FIG. 3, the detecting section 20 is allowed to have a structure such that a detection arm 21 is connected to the auxiliary member 17, and that a contact 22 provided at the distal end portion of the arm 21 can be brought into press contact with a load detector 23 such as a load cell. Further, the detecting section 20 contains a converter 24. As shown in the block chart of FIG. 5 illustrating the measuring means 10 as a block, the converter 24 has reference voltage setting means 25 which supplies a reference voltage to the load detector 23; conversion means 26 which converts a DC voltage signal from the load detector 23 into a DC current signal; and range selecting means 27 and range shifting means 28 which function respectively for range setting in the signal conversion by the conversion means 26.

The property determining apparatus 1 is used by connecting the connecting opening 2w of the sampling cylinder 2, for example, to a transfer pipe P of a slurry material such as sludge and pulp slurry to perform measuring action as follows. In the state where the measuring action is not started yet, the quantitative sampling piston pair is positioned at an initial position with a sampling volume securing space S being defined between the rear piston 3 and the front piston 4, as depicted by the two-dot chain line in FIG. 1. That is, the rear piston 3 is locating at the connecting opening 2w, and the front piston 4 is protruded into the transfer pipe P. In this initial state, if the operation rod 6 of the air cylinder 5 is retracted to pull back the quantitative sampling piston pair, the front and rear pistons 4,3 retract synchronously with the space S being maintained between them to collect a predetermined amount of slurry material corresponding to that space S from the transfer pipe P into the sampling cylinder 2.

When the quantitative sampling piston pair assuming such state is further retracted, the rear piston 3 is abutted against a step-like stopper portion 29 formed on the inner circumference of the sampling cylinder 2. As a result, the rear piston 3 is stopped there, and holding of the rear piston 3 by the holding means 7 is also released. Thereafter, only the front piston 4 retracts to narrow gradually the space between these pistons 3 and 4. Thus, the slurry material confined in the space defined by the pistons 3,4 and the sampling cylinder 2 is, compressed and forced out of this space through the communication openings 2h,8h and fed into the measurement tank 8 in a flowing manner. It should be noted here that, as shown in FIG. 1, at a point that the rear piston 3 is abutted against the stopper portion 29, the front piston 4 is locating at a position indicated by the two-dot chain line, whereas in the state where the pistons 3 and 4 are defining a minimum space, the front piston 4 is locating at a position indicated by the solid line. In this state, the holding means 7 is retracted to the position indicated by the solid line.

When suitable detecting means detects that a predetermined amount of slurry material is supplied to the measurement tank 8, the measuring means 10 is actuated to carry out determination. For such purpose, the electric motor 13 is energized to rotate the rotor 12 in the slurry material supplied to the measurement tank 8 as described above. As the rotor 12 is rotated in the slurry material, viscosity resistance of the slurry material is detected as a reaction force to be generated by this rotation. If the slurry material is, for example, a sludge, its solid content level, flocculation degree, floc strength, etc. can be, as necessary, determined from the thus measured viscosity resistance value, as will be described later.

After completion of the measurement by the measuring means 10, the air cylinder 5 is operated contrariwise to advance the operation rod 6. Thus, only the front piston 4 advances first to widen again the space between the pistons 3 and 4. Consequently, the slurry material flows back contrariwise from the measurement tank 8 into the space defined by the pistons 3,4 and the sampling cylinder 2. In this state, if the operation rod 6 is advanced further, the rear piston 3 stopped by the stopper portion 29 is held by the holding means 7, and then the pistons 3,4 advance synchronously to the initial position with the space S to return the slurry material into the transfer pipe P. After the slurry material is discharged as described above, a wash water is introduced by a cleaning mechanism to clean the inside of the measurement tank 8 and that of the sampling cylinder 2 to complete one measurement cycle. This washing operation is preferably conditioned, for example, by an electric circuit to be performed surely after each cycle is completed to ensure that the next measurement run may not be affected by the residual slurry material. In addition, the washing water resulted after cleaning of the measurement tank 8 and the like is discharged to the outside of the system through a discharge valve 30 so as to prevent the slurry material treating system to be measured from being affected by the washing.

Figure 6:
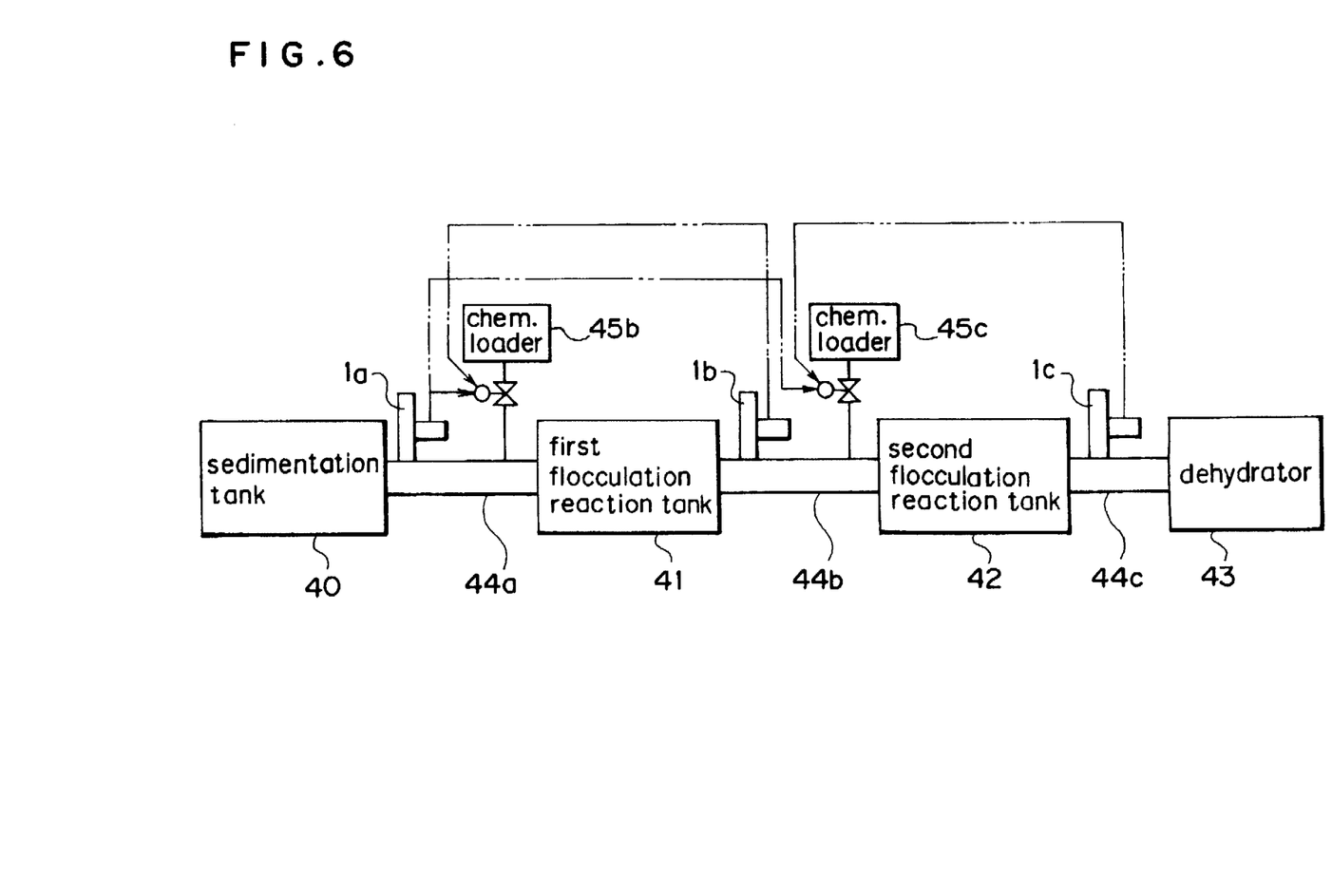
FIG. 6 shows a constitutional view of a sludge treating system according to one embodiment of the present invention.

Next, one embodiment of the sludge treating system employed for embodying the sludge treating process according to the present invention will be described. The sludge treating system in this embodiment has a constitution as shown in FIG. 6. This system contains a sedimentation tank 40 as a raw sludge storage tank, a first flocculation reaction tank 41, a second flocculation reaction tank 42, a dehydrator 43 and transfer passages 44a,44b,44c connecting them. The system also contains chemical loaders 45b,45c connected to the transfer passages 44a,44b locating upstream the first and second flocculation reaction tanks 41,42, respectively and also property determining apparatuses 1a,1b,1c, like the one as described above, connected to the transfer passages 44a,44b,44c, respectively.

In the sedimentation tank 40, sludge is settled and separated from polluted water. The sludge settled in the sedimentation tank 40 is fed through the transfer passage 44a to the first flocculation reaction tank 41, where the sludge is subjected to a primary flocculation treatment by adding the sludge, for example, a cation type flocculating agent from the chemical loader 45b. The chemical loader 45b is, for example, allowed to have a structure in which the flocculating agent is added via an automatically controllable valve mechanism such as a proportional control valve, so that the automatically controllable valve mechanism may be automatically controlled based on the measurement data fed from the property determining apparatuses 1a,1b. The property determining apparatus 1a measures solid content level of the sludge from the sedimentation tank 40, i.e. of the raw sludge, to feed data obtained here as feed-forward automatic control data to the chemical loaders 45b,45c (depicted by the one-dot chain line arrow in FIG. 6), whereas the property determining apparatus 1b measures flocculation degree of the primarily flocculated sludge formed after treatment in the first flocculation reaction tank 41 to feed the date obtained here as feed-back automatic control data to the chemical loader 45b (indicated by the two-dot chain line arrow in FIG. 6).

The primarily flocculated sludge obtained after the primary flocculation treatment in the first flocculation reaction tank 41 is fed through the transfer passage 44b into the second flocculation reaction tank 42, where the sludge is subjected to a secondary flocculation treatment by adding thereto, from the chemical loader 45c, an anion type flocculating agent having a charge opposite to the case of the first flocculation reaction tank 41. This chemical loader 45c, like the chemical loader 45b, is also subjected to feed-forward control based on the measurement data fed from the property determining apparatus 1a, and is also subjected to feed-back control based on the measurement data of sludge floc strength measured by the property determining apparatus 1c (indicated by the two-dot chain line arrow in FIG. 6).

The secondarily flocculated sludge is fed from the second flocculation reaction tank 42 through the transfer passage 44c to the dehydrator 43 where the sludge is subjected to dehydration treatment to form a sludge cake.

Figure 7:
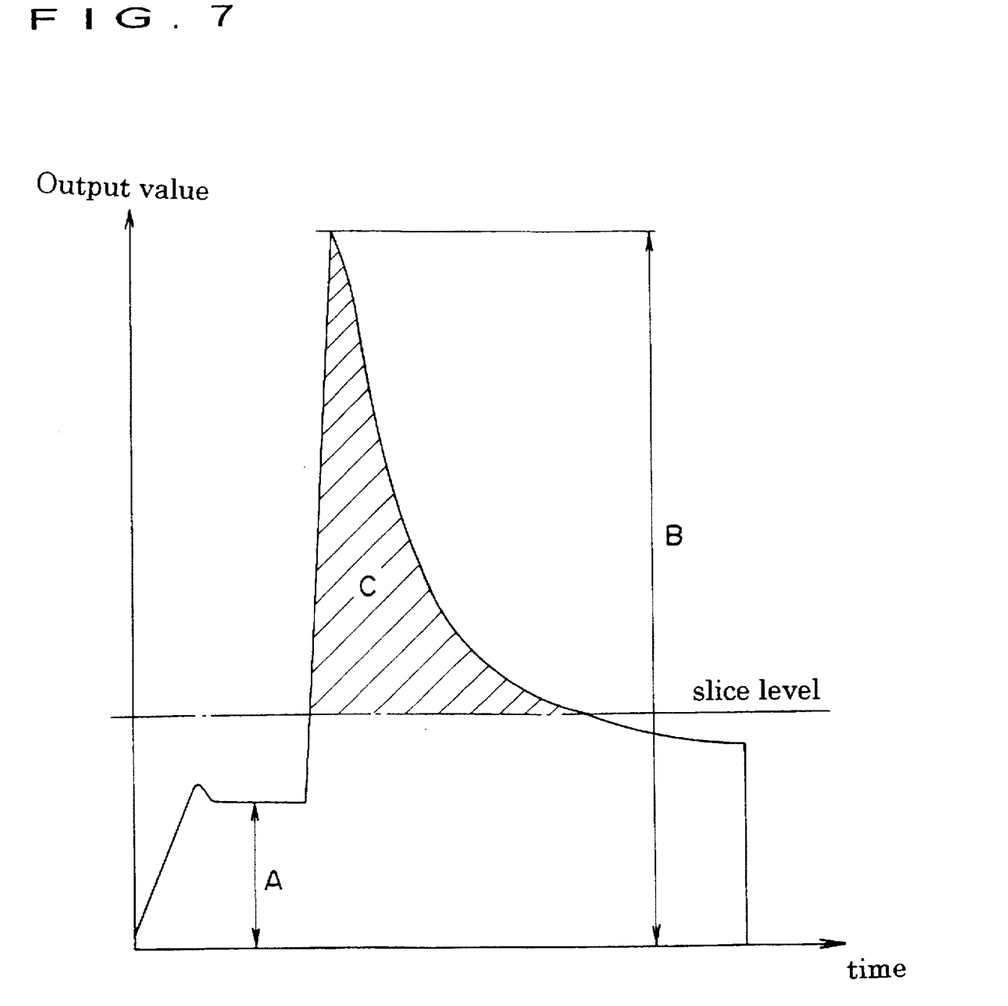
FIG. 7 is a graph showing change in the output value with time in the measuring means of the property determining apparatus.

Now, the principle that the property determining apparatuses 1a,1b,1c determine sludge solid content level, sludge flocculation degree and sludge floc strength respectively will be described briefly. FIG. 7 is a graph illustrating change in the output value of the measuring means 10 with time; in which A represents concentration, and the higher the index is, the higher the concentration is; B represents flocculation degree, and the higher the peak value is, the higher the flocculation degree is; and C represents area obtained by integrating values of flocculation degree above the slice level, and the greater the area is, the higher the floc strength is. As the graph shows, any of the solid content level, flocculation degree and floc strength can be obtained depending on which of the values A,B,C is to be determined.

Figure 8:
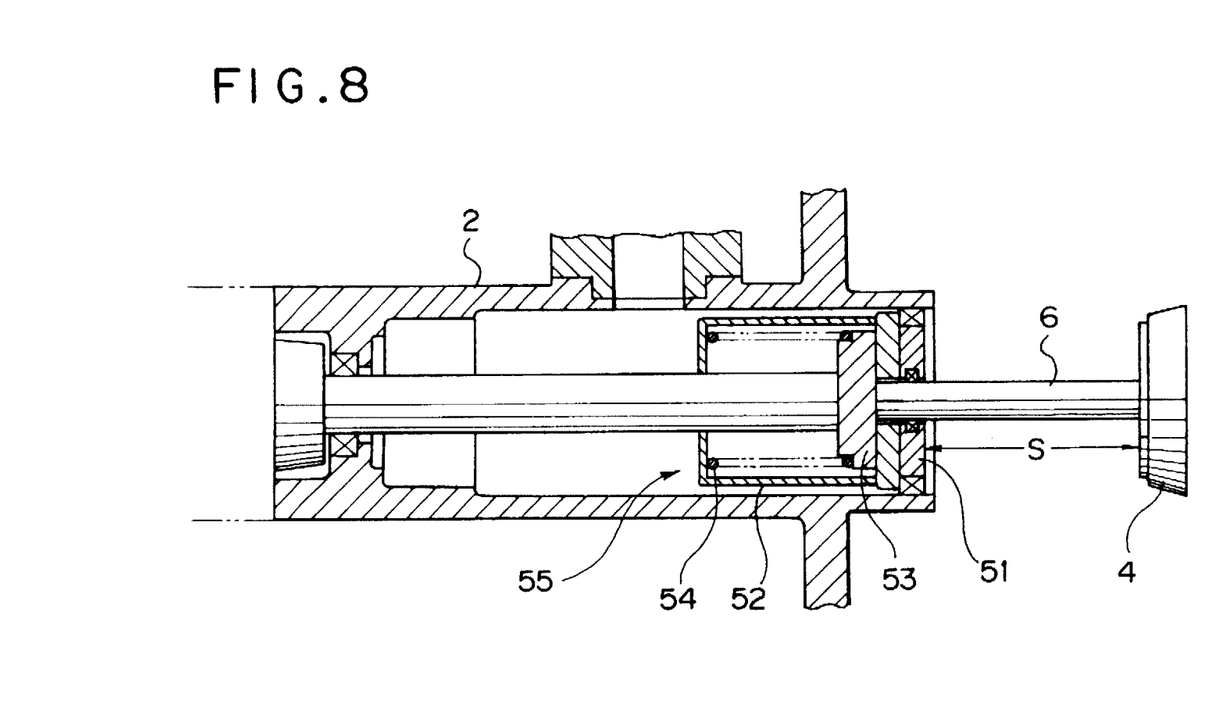
FIG. 8 shows a cross-sectional view of a major section of the property determining apparatus according to a second embodiment of the present invention.
Figure 9:
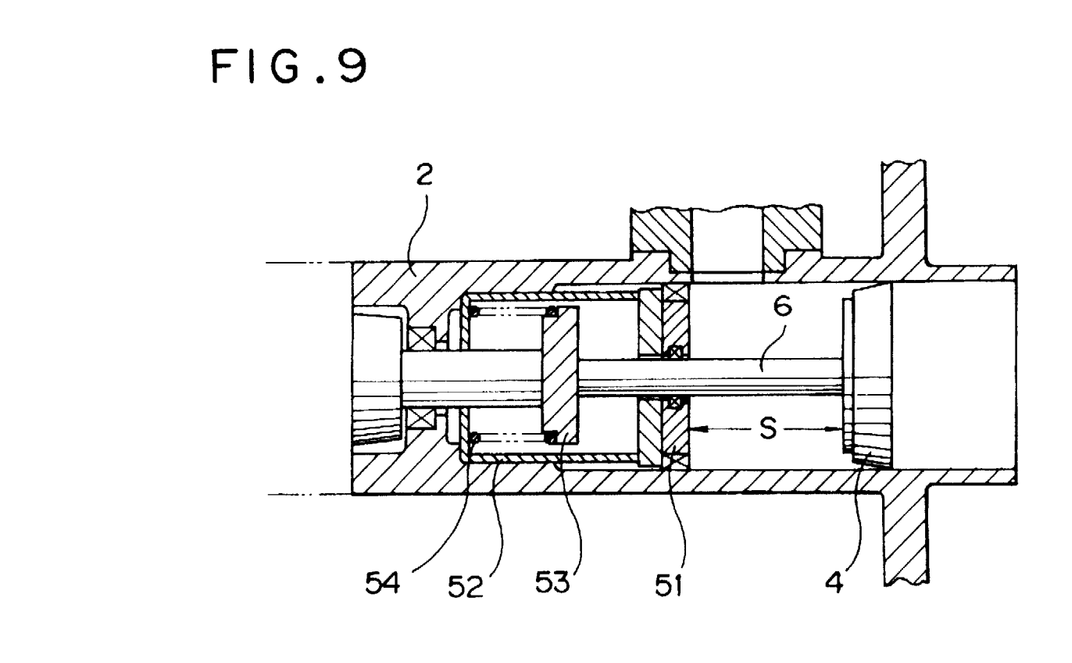
FIG. 9 shows a cross-sectional view of the major section shown in FIG. 8, in which the front and rear pistons are retracted.

Other embodiments of the property determining apparatus according to the present invention will be described below. First, referring to a second embodiment of the property determining apparatus, the major section of which is shown in FIG. 8, the apparatus is provided with retaining means 55 consisting of a cylindrical spring holder 52 extended backward from the rear surface of a rear piston 51, a holding plate 53 fixed to the operation rod 6 and a spring 54 which pushes the holding plate 53 in the spring holder 52 to urge the rear piston 51 to be brought into intimate contact with the holding plate 53. This holding means 55 plays the role of the holding means 7 in the property determining apparatus in the first embodiment described above. Specifically, when the rear piston 51 is retracted with a predetermined space being defined together with the front piston 4 so as to provide a sampling volume securing space S and to collect a predetermined amount of slurry material into the sampling cylinder 2, the retracting force of the operation rod 6 is transmitted to the rear piston 51 by the urging force of the spring 54. Further, as shown in FIG. 9, when the rear piston 51 is retracted to the predetermined position, the spring holder 52 is abutted against the inner extremity of the sampling cylinder 2, and, in this state, the operation rod 6 is retracted further compressing the spring 54 to reduce the sampling volume securing space S.

Figure 10:
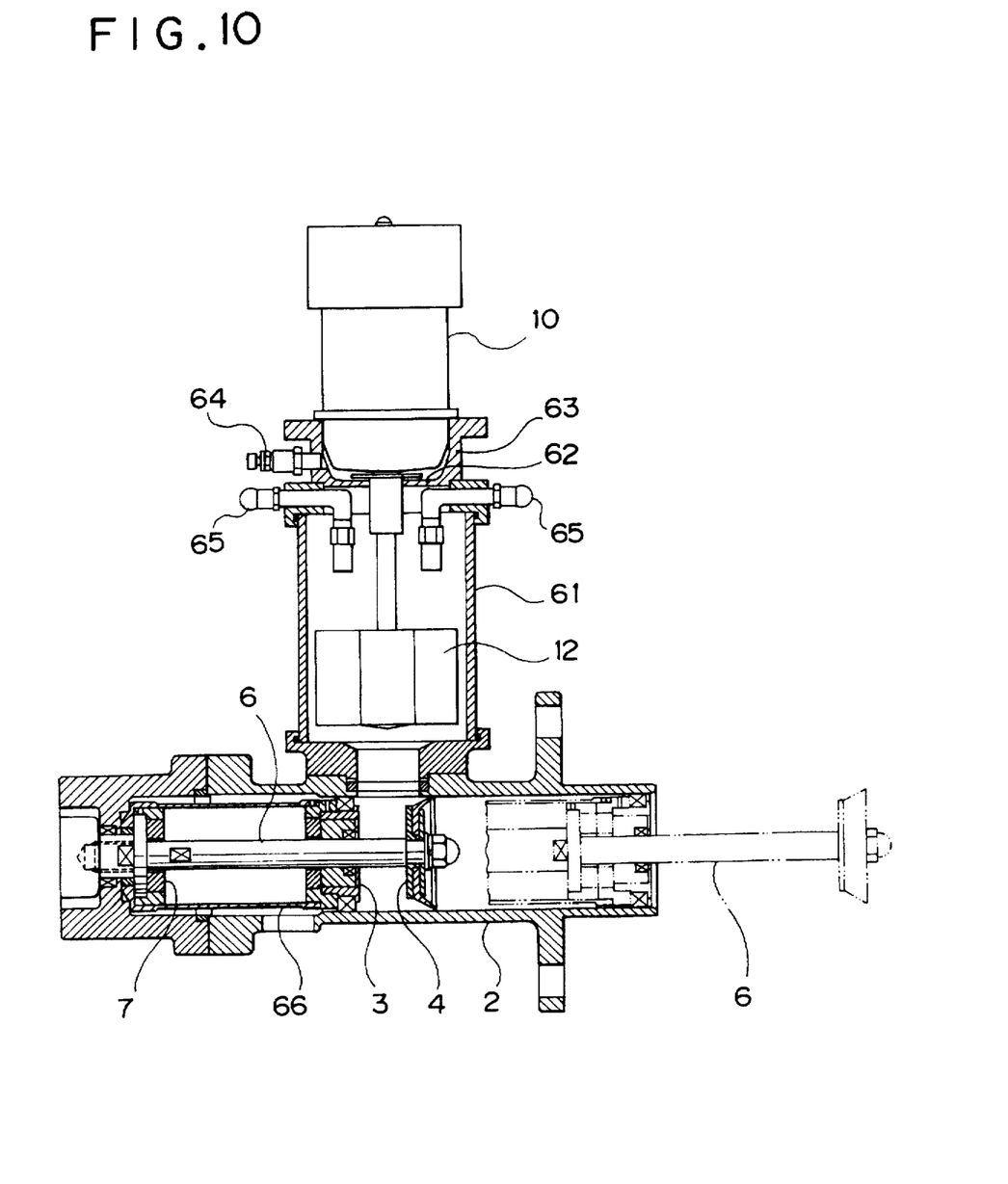
FIG. 10 shows a cross-sectional view of a major section of the property determining apparatus according to a third embodiment of the present invention.

Next, according to a third embodiment of the present invention, the property determining apparatus is of a structure having a major section as shown in FIG. 10. More specifically, a measurement tank 61 is provided with a mounting socket 63 having a partition 62 which separates the socket 63 from the below tank 61, and the measuring means 10 is airtightly mounted on this socket 63. An air supply nozzle 64 is attached to the mounting socket 63, and a pair of air supply nozzles 64,65 are attached to the measurement tank 61 below and adjacent to the mounting socket 63, so that high-pressure air may be, for example, sprayed into the mounting socket 63 and the measurement tank 61 through these air supply nozzles 64 and 65 respectively. Such high-pressure air should be interlockedly injected with the operation of the measuring means 10 as described above. The thus injected compressed air prevents the slurry material stirred by the rotor 12 as it rotates from scattering toward the driving mechanism side of the measuring means 10. In other words, if the slurry material is scattered upward to adhere on the driving mechanism and the like of the measuring means 10, operability of the measuring means 10 is liable to be impaired, so that the high-pressure air is injected so as to prevent the slurry material from scattering upward.

In this embodiment, the rear end portion of the rear piston 3 and the holding means 7, having the same structures as in the first embodiment respectively, are covered with a cover cylinder 66. This cover cylinder 66 also serves to prevent the slurry material collected into the sampling cylinder 2 from adhering to the rear surface of the rear piston 3 and the holding means 7 and to provide more stable operability.

As has been described heretofore, the present invention enables real-time determination of properties of a slurry material sampled directly out of a slurry transfer passage and the like any time as necessary, and the present invention greatly promotes, for example, realization of economical and energy-saving sludge treatment or improvement of the function of a pulp concentration adjusting system in a pulp treatment line. The present invention adds flocculating agents in a controlled manner under optimum conditions depending on the properties of the sludge based on data available through the property-determining apparatuses capable of determining properties of a sludge under treatment in real time, which can provide economical and energy-saving sludge treatment.

Although only three embodiments of the present invention have been described herein, it should be apparent to those skilled in the art that the present invention may be embodied in many other specific forms without departing from the spirit or scope of the invention. Therefore, the present examples and embodiments are to be considered as illustrative and not restrictive, and the invention is not to be limited to the details given herein, but may be modified within the scope of the appended claims.

What is claimed is:

1. A property determining-apparatus for determining solid content level, flocculation degree or other properties of a slurry material such as sludge and pulp slurry sampled directly out of a slurry transfer passage or a slurry storage tank, said apparatus comprising:

a sampling cylinder having a connecting opening at one end;

a quantitative sampling piston pair having a front piston and a rear piston which are accommodated in said sampling cylinder;

operating means for operating said quantitative sampling piston pair;

a measurement tank connected to said sampling cylinder; and measuring means incorporated into said measurement tank;

wherein said apparatus is used with the connecting opening of said sampling cylinder connected to said transfer passage; said quantitative sampling piston pair is positioned at an initial position with a sampling volume securing space being defined between said front and rear pistons; said quantitative sampling piston pair assuming such state is retracted to collect a slurry material from said transfer passage in a volume corresponding to said sampling volume securing space into said sampling cylinder; the space between said front and rear pistons is narrowed to force said slurry material in said sampling cylinder to be fed into said measurement tank; property of said slurry material in said measurement tank is measured by said measuring means; the space between said front and rear pistons is widened to resume the original width after completion of the measurement to return said slurry material in said measurement tank into said sampling cylinder; and said quantitative sampling piston pair is advanced to said initial position to return said slurry material in said sampling cylinder into said transfer passage.

2. The property determining apparatus according to claim 1, wherein said measuring means contains a rotor which, when rotated, determines the property of said slurry material by measuring viscosity resistance exerted to said rotor.

3. The property determining apparatus according to claim 1, wherein the operating means of said quantitative sampling piston pair is composed of an operating body having an operation rod which advances and retracts along the axis of said sampling cylinder, said rear piston is penetrated with the operation rod and held, when required, by holding means fixed to said operation rod, while said front piston is unmovably connected to said operation rod; said quantitative sampling piston pair is retracted with said rear piston being held by said holding means in the stroke that said slurry material is to be collected, and when said quantitative sampling piston pair is retracted to a predetermined position where said rear piston is abutted against a stopper portion formed in said sampling cylinder, holding of said rear piston by said holding means is released; and said front piston assuming such state is further retracted to narrow the space between said front piston and said rear piston.

\* \* \* \* \*